United States Patent [19]

Ogawa et al.

[11] Patent Number: 4,990,604

[45] Date of Patent: Feb. 5, 1991

[54] ASIALOGANGLIOSIDE RELATED COMPOUNDS

[75] Inventors: Tomoya Ogawa, Tokyo; Mamoru Sugimoto, Niiza; Yoshiyasu Shitori, Tokyo; Toshio Horisaki, Wako; Tadami Shinuchi, Kyoto, all of Japan

[73] Assignees: Rikagaku Kenkyusho, Wako; Kanto Ishi Pharmaceutical Co., Ltd., Tokyo; Teikoku Chemical Industry Co., Ltd., Osaka, all of Japan

[21] Appl. No.: 832,574

[22] Filed: Feb. 24, 1986

[30] Foreign Application Priority Data

Apr. 2, 1985 [JP] Japan .................................. 60-69743

[51] Int. Cl.$^5$ ............................................... C07H 5/06
[52] U.S. Cl. .................................. 536/17.9; 536/17.2; 536/123
[58] Field of Search ...................... 536/17.9, 17.2, 4.1, 536/123

[56] References Cited

PUBLICATIONS

Migrdechian, *Organic Synthesis*, vol. 1, 1957; pages 39 and 429.
Sugimoto et al., *Glycoconjugate J.* (1985), vol. 2, pp. 11–15.
March, *Advanced Organic Chemistry: Reactions Mechanisms and Structure*, 1968, pp. 669.
The Merck Index, 9th ed., 1976, p. 562; No. 4201.
Young et al., *Chemical Abstracts*, vol. 92, No. 144763y (1980).
Urdal et al., *Chemical Abstracts*, vol. 93, No. 210472 (1980).
Wessel H-P, Iversen T, Bundle DR (1984) Carbohydr. Res. 130:5–21.
Sabesan S., Lemieux RU (1984) Can. J. Chem. 62:644–54.
Paulsen H., Paal M., Hadamczyk D., Steiger K-M (1984), Carbohydr. Res. 131:C1–C5.

*Primary Examiner*—Johnnie R. Brown
*Assistant Examiner*—Elli Peselev
*Attorney, Agent, or Firm*—Oblon, Spivak, McClelland, Maier & Neustadt

[57] ABSTRACT

Method for the production of asialoganglioside related compounds of the formula (I).

wherein $R^1$ is hydrogen or benzoyl, $R^2$ is hydrogen or acetyl, $R^3$ is hydrogen, acetyl, $\beta$-D-galactopyranosyl or 2,3,4,6-tetra-O-acetyl-$\beta$-D-galactopyranosyl, $R^7$ and $R^8$ are individually alkyl having 1 to 30 carbon atoms and Ac is acetyl.

6 Claims, No Drawings

ASIALOGANGLIOSIDE RELATED COMPOUNDS

BACKGROUND OF THE INVENTION

(1) Field of the Invention

This invention relates to asialoganglioside related compounds, and emore particularly to methods for producing asialo $G_{M1}$, asialo $G_{M2}$ and intermediate compounds for use in producing the same.

(2) Description of the Prior Art

Glycolipids found in mammal cells are glycosides between ceramides, which are sphingosines (long chain amino alcohols) to which aliphatic acids have been attached through an amide linkage, and one or more sugars such as glucose, galactose, N-acetyl glucosamine, N-acetyl galactosamine, fucose, sialic acid, etc. Among these glycosides, those containing sialic acid are called gangliosides.

Compounds obtained by removing sialic acid residue from gangliosides are called asialoganglioside, which are naturally found in a smaller amount than gangliosides, and therefore which have been prepared by hydrolysis of corresponding gangliosides with formic acid or sialidase.

Asialo-$G_{M1}$-ganglioside or gangliotetraosylceramide 1 was reported to be present as a rat erythrocyte antigen and as a mouse natural killer cell marker (1). Antibodies directed to asialo-$G_{M1}$-ganglioside have been used to detect acute lymphatic leukemia cells (1). The structure of 1 was determined by partial degradation and methylation analysis (2-4). Asialo-$G_{M2}$-ganglioside or gangliotriosylceramide 24 has been isolated from the brain of a Tay-Sachs patient (1), guinea pig erthrocytes (5), mouse Kirsten tumor (6), and rat hepatoma (7).

Due to their functions as tumor-associated markers, three independent approaches to the synthesis of the glycan part of asialo-$G_{M1}$- and asialo-$G_{M2}$-ganglioside have recently been reported (8–10).

1. Hakomori S. (1983) in Handbook of Lipid Research, Vol 3, Sphingolipid Biochemistry, eds. Kanfer J. N., Hakomori S., Plenum Press, New York, p 121–29.
2. Svennerholm L. (1962) Biochem Biophys Res Commun. 9:436–41.
3. Kuhn R., Wiegandt H. (1963) Chem. Ber. 96:866–80.
4. Kuhn R., Egge H. (1963) Chem. Ber. 96:3338–48.
5. Seyama Y., Yamakawa T. (1974) J. Biochem. (Tokyo) 75:837–42.
6. Rosenfelder G., Young W. W. Jr. Hakomori S. (1977) Cancer Res. 37:1333–39.
7. Hirabayashi Y., Taki T., Matsumoto M., Kojima K. (1978) Biochim. Biophys. Acta 529:96–105.
8. Wessel H-P., Iversen T., Bundle D. R. (1984) Carbohydr. Res. 130:5–21.
9. Sabesan S., Lemieux R. U. (1984) Can. J. Chem. 62:644–54.
10. Paulsen H., Paal M., Hadamczyk D., Steiger K-M. (1984) Carbohydr. Res. 131:C1–C5.

As mentioned above, asialogangliosides exist mainly in the outer surfaces of bilayer of mammal cell membranes. Recent studies show that gangliosides play important roles in reception and recognition of, and response to, information in cells, receptor mechanism, differentiation, cell propagation, malignant cell transformation, cell behavior, etc.

However it is very difficult to isolate asialogangliosides from an organism in which they exist in a smaller amount. Therefore precise synthesis of such asialogangliosides is necessary for the elucidation of the precise correlation between biological information and the molecular structure of the oligosaccharides.

SUMMARY OF THE INVENTION

An object of this invention is therefore to provide methods for the production of asialogangliosides and related compounds thereof which can be intermediate compounds for use in producing asialogangliosides.

The asialoganglioside related compounds of this invention is represented by the formula (I).

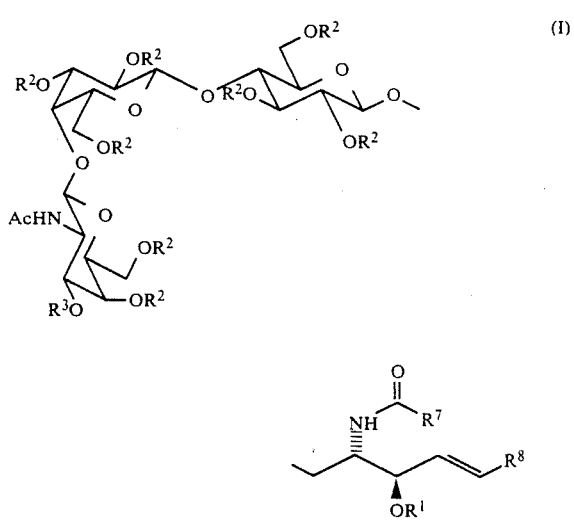

wherein $R^1$ is hydrogen or benzoyl, $R^2$ is hydrogen or acetyl, $R^3$ is hydrogen, acetyl, $\beta$-D-galactopyranosyl or 2,3,4,6-tetra-0-acetyl-$\beta$-D-galactopyranosyl, $R^7$ and $R^8$ are individually alkyl having 1 to 30 carbon atoms and Ac is acetyl.

DETAILED DESCRIPTION OF THE INVENTION

Specific examples of the compounds of this invention represented by the formula (I) include:

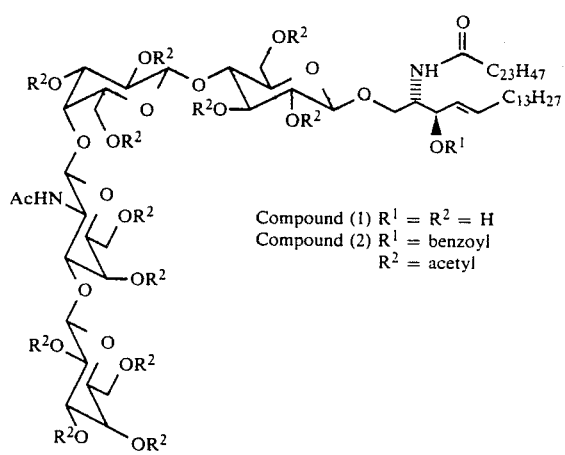

Compound (1) $R^1 = R^2 = H$
Compound (2) $R^1$ = benzoyl
$R^2$ = acetyl

-continued

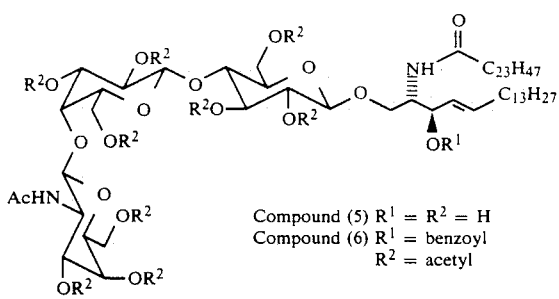

Compound (5) R¹ = R² = H
Compound (6) R¹ = benzoyl
R² = acetyl

This invention further provides a method for the production of the following compounds:

Compound (3)
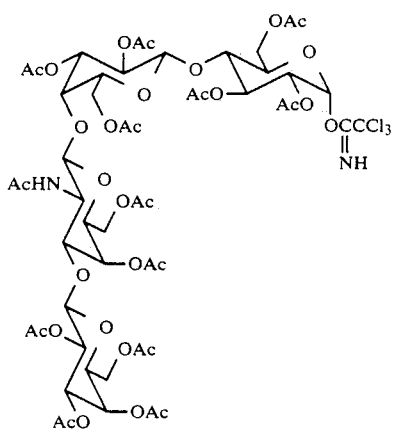

Compound (4)
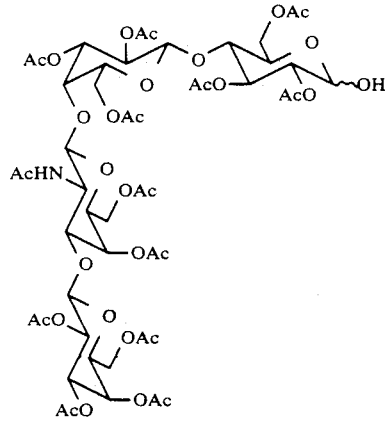

Compound (7)
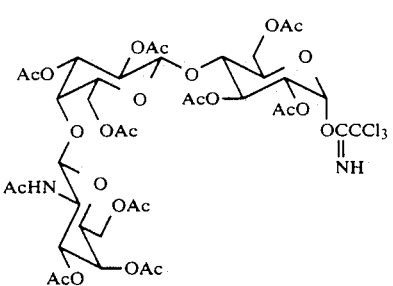

-continued

Compound (8)
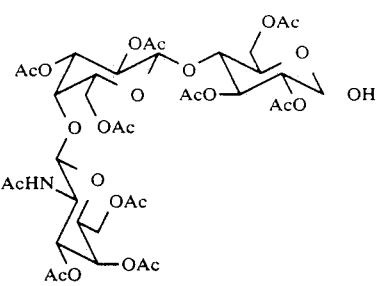

The above-mentioned compounds can be produced by a method which comprises treating the compounds (9) or (10) of the formula:

(9) or (10)
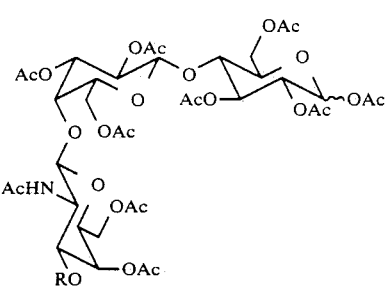

wherein R represents 2,3,4,6-tetra-0-acetyl-β-D-galactopyranosyl (the compound (9)) or acetyl (the compound (10)) and Ac represents acetyl, with hydrazinium acetate to obtain the compound (4) or (8), which is then reacted with trichloroacetonitrile in the presence of alkali metal hydride such as NaH to obtain the compound (3) or (7), which is in turn reacted with a ceramide of the formula (11):

(11)
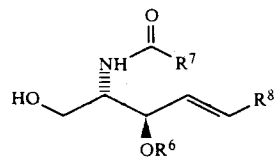

wherein $R^6$ is a protective group such as benzoyl and $R^7$ and $R^8$ are individually alkyl having 1 to 30 carbon atoms, and if necessary, removing protective groups such as acetyl or benzoyl. When the compound (12) of the formula (11) wherein $R^7$ is $C_{23}H_{47}$ and $R^8$ is $C_{13}H_{27}$ is used, the compounds (1) and (2) are obtained. One example of the reaction steps is illustrated in Schemes 1 and 2.

Scheme 1
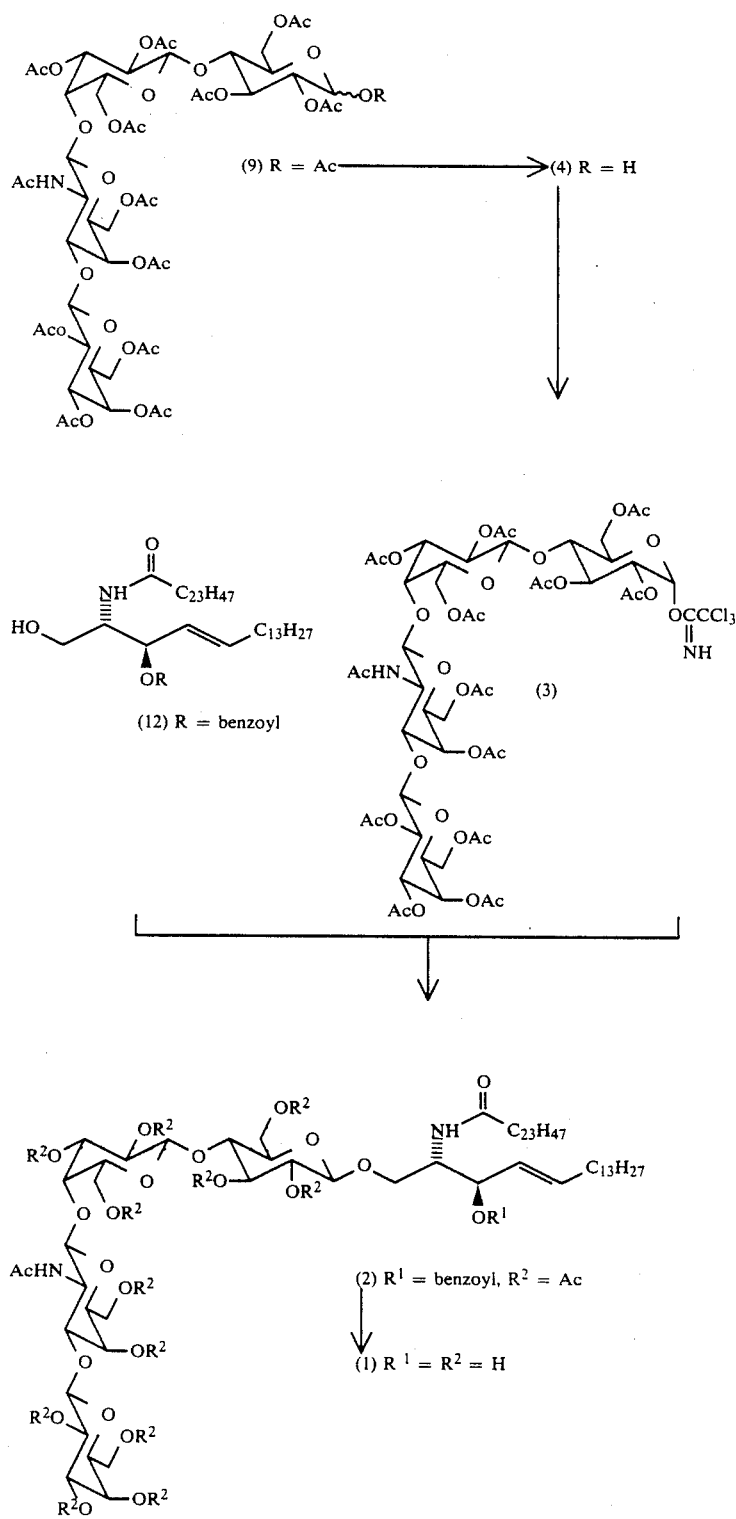

Scheme 2

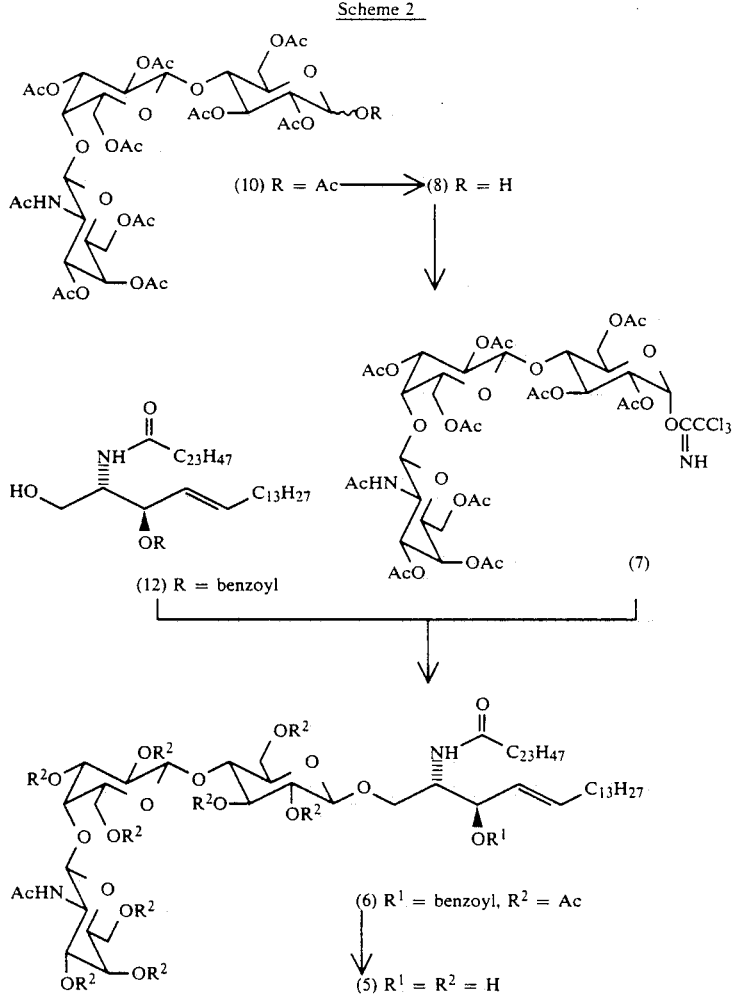

The starting compound (9) can be prepared as follows.

Benzyl penta-O-benzyl-β-D-laotoside (21) is selectively benzylated by the stannyl method (Ogawa T., Matsui M, (1978) Carbohydr. Res 62:C1–C4; (1981) Tetrahedron 37:2363–2369; Veyrieres A., (1981) J. Chem Soc, Perkin Trans 1 1626–1629.) to obtain benzyl hexa-O-benzyl-62 -D-lactoside (22), which is then reacted, in the presence of $AgOSO_2CF_3$ and Molecular Sieves 4A in dichloroethylene, with 3,4,6-tri-O-acetyl-2-deoxy-2-phthalimido-β-D-galactopyranosyl bromide (23) (Lemieux R. U., Ratcliffe R. M., (1979) Can.J.-Chem 57:1244–1251) to obtain trisaccharide (24). The compound (24) is treated with (i) NaOMe—MeOH, (ii) n—$BuNH_2$—MeOH and (iii) $Ac_2O$-pyridine in this order to obtain the compound (25), which is then deacetylated to obtain the compound (26), which is in turn treated with $C_6H_5CH(OMe)_2$ and touluenesulfonic acid (TsOH) in $CH_3CN$ to obtain the benzylidene derivative (27). The compound (27) is reacted with aceto-bromogalactose (28) in benzene-nitromethane in the presence of $Hg(CN)_2$ and Molecular Sieves 4A to obtain the tetrasaccharide (29), which is then treated with 80% acetic acid to obtain the compound (30), which is then debenzylated by catalytic hydrogenation in the presence of Pd-C in acetic acid to obtain the compound (31), which is acetylated with $Ac_2O$/pyridine to obtain the peracetylated tetrasaccharide (9).

The peracetylated trisaccharide (10) can be obtained by catalytic hydrogenation of the compound (25) in the presence of Pd-C in acetic acid to obtain the compound (32), followed by acetylation of the compound (32) with $Ac_2O$/pyridine.

Another starting compound, i.e. the ceramide (11) can be prepared by the method disclosed in Japanese Patent Public Disclosure No. 60-190745.

One example of the synthetic steps for the preparation of the starting compounds (9) and (10) and the compound (12) as a specific example of ceramide (11) is illustrated in Schemes 3 and 4.

Scheme 3
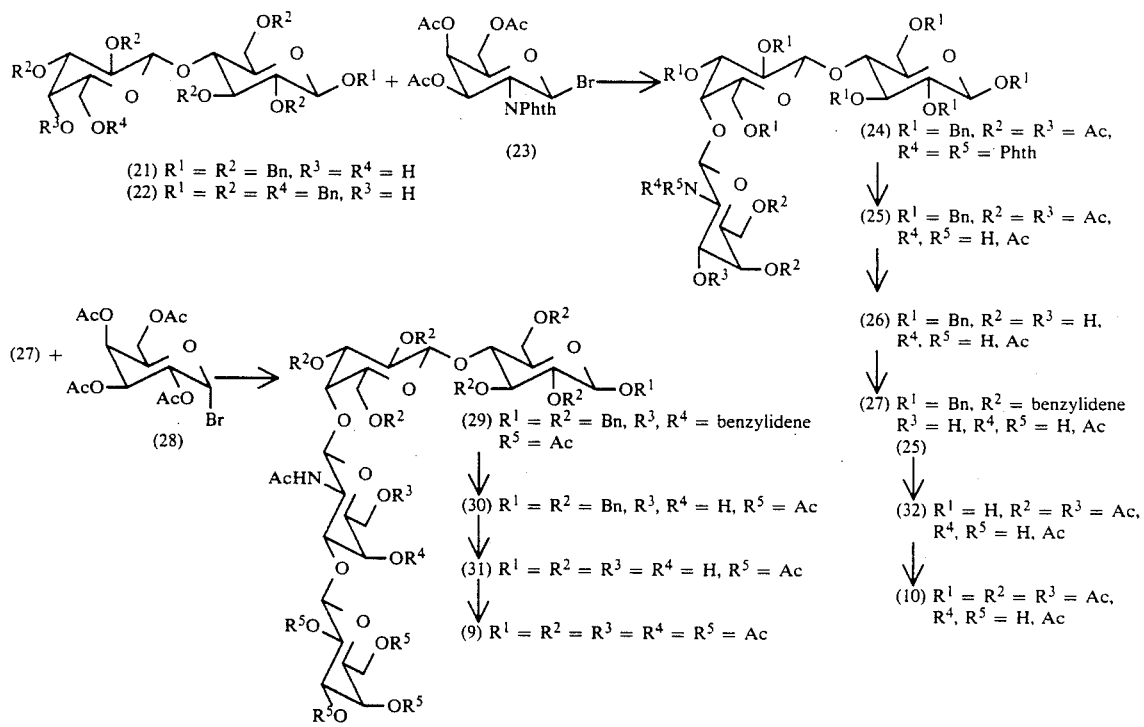
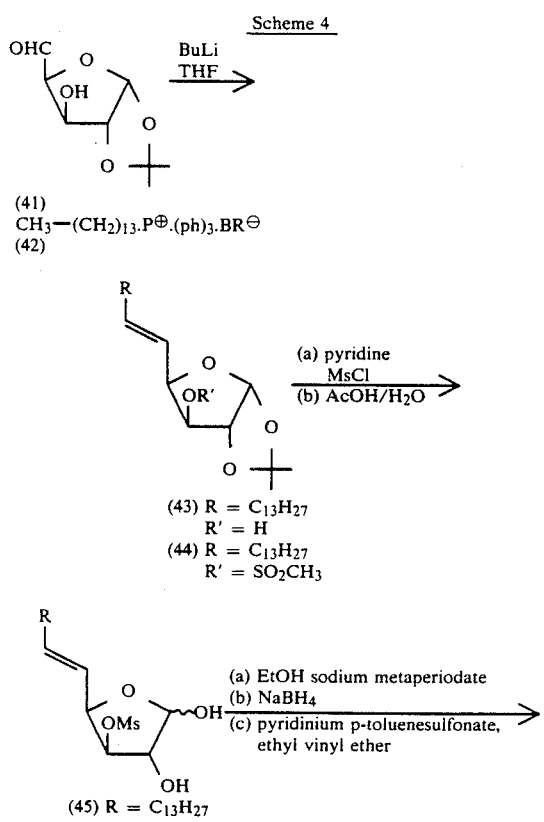
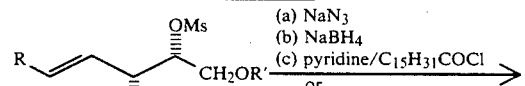
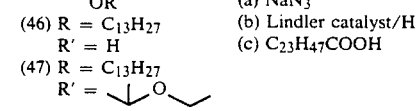
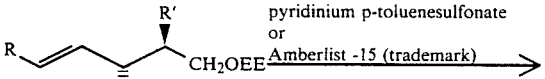
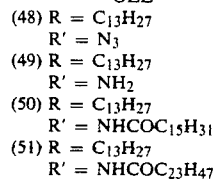
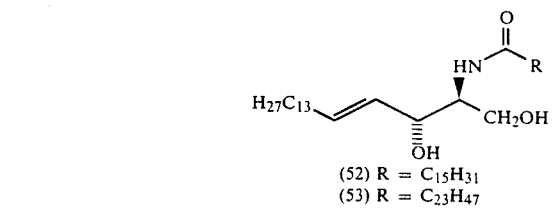
The compound (42) can be obtained by refluxing overnight a solution of alkyl halide such as 1-bromotetradecane and triphenylphosphine in a solvent such as xylene.

1,2-O-isopropylidene-α-D-xylo-pentodialdo-1,4-furanose (41) is reacted with the compound (42) in the presence of BuLi in a solvent such as THF or hexane to prepare the 4-alkylvinyl derivative (43). The reaction temperature and time are suitably −15° C. to 25° C. and 0.5 to 24 hours, respectively.

The compound (43) is treated with methanesulfonyl chloride in dry pyridine to produce the 3-methanesulfonyl derivative (44). The reaction is suitably carried out at 0°- C. to 25° C. for 2 to 24 hours.

Treatment of the compound (44) in acetic acid/water removes the isopropylidene group therefrom to yield the diol (45). The reaction is suitably carried out at 70° to 90° C. for 0.5 to 5 hours.

The compound (45) is treated with an oxidizing agent such as sodium metaperiodate in a solvent such as ethanol to cut the diol part and then treated with a reducing agent such as sodium borohydride to obtain the diol compound (46). The oxidation is carried out at 0° C. to 25° C. for 0.5 to 24 hours and the reduction at 0° C. to 10° C. for 0.5 to 2 hours.

The compound (46) is reacted with an alkyl vinyl ether such as ethyl vinyl ether in a solvent such as dichloromethane in the presence of a catalyst such as pyridinium p-toluenesulfonate to obtain the di-alkyl vinyl ether (47). This reaction is suitably carried out at 0° C. to 30° C. for 0.5 to 24 hours.

The compound (47) is treated an azide such as sodium adzide in a solvent such as DMF (dimethylformamide) to obtain the compound (48). This reaction is suitably carried out at 70° C. to 120° C. for 12 hours to 6 days.

The azide (48) is treated with a reducing agent such as sodium borohydride or Lindler catalyst/$H_2$ in a solvent such as ethanol or isopropanol to obtain the amine (49). This reaction is suitably carried out at a reflux temperature for 1 to 6 days when sodium borohydride is used and at 0° C. to 30° C. for 2 to 24 hours at a hydrogen pressure of 1 to 4 atoms when Lindler catalyst/$H_2$ is used.

The amine (49) is reacted with an acyl halide in the presence of a basic compound such as pyridine or dimethylaminopyridine to obtain the amide (50) or (51). This reaction is suitably carried out at 0° C. to 30° C. for 0.5 to 24 hours. Alternatively, the amine (49) is dissolved in dichloromethane or the like and reacted with an aliphatic acid in the presence of 2-chloro-1-methylpyridinium iodide, tri-n-butyl amine, etc. to obtain the amide (50) or (51). This reaction is sufficiently carried out at a reflux temperature for 0.5 to 13 hours in an inert gas atmosphere such as argon.

The amide (50) or (51) is then treated with pyridinium p-toluenesulfonate, Amberlist 15 (trademark), etc. in a solvent such as methanol, dichloromethane to remove the protective groups. Thus the ceramide (52) or (53) is obtained.

The compound (53) is treated with tritylchloride in pyridine to obtain the trityl derivative (54), which is then treated with benzoyl chloride/dimethylamino pyridine to obtain the trityl-benzoyl derivative (55) which is in turn treated with p-toluenesulfonic acid to remove the trityl group. Thus, the benzoyl ceramide (12) is obtained. These reactions can be conducted with or without the isolation of the compounds (54) and (55).

The compound (9) or (10) is treated with $NH_2NH_2$—AcOH to remove only the glycosyl acetyl and the compound (4) or (8) is obtained (Excoffier G., Gagnaire D., Utille J-P., (1975) Carbohydr. Res. 39:368–373). The compound (4) or (8) is treated with trichloroacetonitrile/NaH according to the Schmidt et al method to obtain the sugar donor (3) or (7) (Schmidt R. R., Michel J. (1980) Angew Chem Int Ed Engl 19:731–732; Schmidt R. R., Michel J., Roos M., (1984) Liebigs Ann. Chem 1343–1357.).

The compound (3) or (7) is reacted with the ceramide (12) in the presence of a glycosidation catalyst such as $BF_3.Et_2O$ and molecular sieves 4A to obtain the protected asialoganglioside $G_{M1}$ (2) or $G_{M2}$ (6), which is treated with MeONa etc. in MeOH—THF to remove acetyl and benzoyl groups. Thus, free asialoganglioside $G_{M1}$ (1) or $G_{M2}$ (5) is obtained.

UTILITY OF THIS INVENTION

Novel compounds (1), (2), (3), (4), (7) and (8) of this invention are useful as a tumor marker, a differentiation marker of cells having differentiation potency, or intermediate compounds for use in the synthesis of such marker.

According to this invention, these useful compounds can be stereoselectively prepared in high yield.

EXAMPLES

This invention will explained more concretely with reference to the following EXAMPLES and REFERENCE EXAMPLES.

Reference Example 1

A solution of the compound (21) (10.6 g, 12 mmole) and bis-tributyl tin oxide (5.36 g, 9 mmole) dissolved in 50 ml toluene was agitated at 140° C. for 4 hours to azeotropically remove water and then distilled until the volume of toluene became 10 ml. To this solution, benzyl bromide (50 ml) and tetrabutylammonium bromide (1.9 g, 6 mmole) were added and agitated overnight at 90° C. in an argon atmosphere.

After the reaction, the mixture was concentrated and dried. The residue was dissolved in dichloromethane. To this solution, cold sodium bicarbonate aqueous solution, potassium fluoride and Celite (trademark) were added and vigorously stirred. Insolubles were filtered off. Ethyl acetate was added. An organic solvent layer was concentrated. The residue was redissolved in dichloromethane. The solution was washed with aqueous KF solution and concentrated. The residue was dissolved in ethyl acetate and insolubles were filtered off. The solution was concentrated and then subjected to column chromatography and eluted with toluene-ethyl acetate (9:1 v/v) to obtain the compound (22) (10.4 g, 89.0%).

(The compound (22))

| Analysis ($C_{61}H_{64}NO_{11}$ = 973.183) | | |
|---|---|---|
| | Calcd. | Found. |
| C | 75.29 | 75.14 |
| H | 6.63 | 6.66 |
| N | 1.01 | 1.03 |

$[\alpha]_D^{19} + 22.10°(C=0.525, CHC_3)$.

Reference Example 2

To well heat-dried molecular sieves 4A powder (15 g), silver triflate ($AgOSO_2CF_3$) (2.62 g, 10.2 mmole) was added. To this mixture, a solution of the compound (22) (4.96 g, 5.1 mmole) in 1,2-dichloroethane (50 ml) and then a solution of the compound (23) (3.81 g, 7.65 mmole) in 1,2-dichloroethane (30 ml) were dropwise added and stirred overnight at room temperature. To this mixture, a solution of the compound (23) (1 g, 2.0 mmole) in 1,2-dichloroethane (10 ml) was added at 0° C. and stirred for 10 hours at room temperature, thereafter silver triflate (0.77 g, 3.0 mmole) was added and stirred overnight. Insolubles were filtered off and 1,2-dichloroethane layer was washed with $NaHCO_3$ water and then saturated NaCl water and then dried on $MgSO_4$. After $MgSO_4$ was filtered off, the solvent was distilled. The residue was subjected to column chromatography and eluted with toluene-ethyl acetate (7:1, v/v) to obtain the compound (24) (5.646 g, 79.6%) and the -anomer thereof (0.521 g, 7.3%).

(The compound (24))

| Analysis ($C_{81}H_{83}NO_{20}$ = 1390.56) | | |
|---|---|---|
| | Calcd. | Found. |
| C | 69.96 | 69.91 |
| H | 6.02 | 5.97 |
| N | 1.01 | 1.03 |

RF (toluene - EA=3.1) 0.48 (α-anomer 0.52 ).
$[α]_D^{19}$ +22.34°(C=0.70, $CHCl_3$).

Reference Example 3

To a solution (100ml) of the compound (24) (5.59 g, 4.0 mmole) in methanol, 0.1N NaOMe (10 ml) was added under ice-cooled condition and stirred at room temperature for 3 hours. The reaction mixture was concentrated. The residue is dissolved in methanol (150 ml). n-Butylamine (30 ml) was added and refluxed at 100° C. for 2 days. The mixture was concentrated and azeotropic distillation was conducted with methanol, toluene and pyridine, thereafter pyridine (100 ml) and acetic anhydride (100 ml) were added and stirred overnight at room temperature. The reaction mixture was concentrated and azeotropic distillation was carried out with ethanol and toluene. The residue was subjected to column chromatography and eluted with toluene-ethyl acetate (3:2, v/v) to obtain the compound (25) (4.74 g, 90.5%).

(The compound (25))

| Analysis ($C_{75}H_{83}NO_{19} \cdot 2H_2O$ = 1338.525) | | |
|---|---|---|
| | Calcd. | Found. |
| C | 67.30 | 66.96 |
| H | 6.55 | 6.18 |
| N | 1.05 | 1.04 |

Rf 0.50 (toluene - EA=1:1).
$[α]_D^{19}$+9.33°(C=0.15, $CHCl_3$).

Reference Example 4

To a solution (10 ml) of the compound (25) (495.3 mg, 0.38 mmole) in methanol, 0.1 N NaOMe (1 ml) was added at 0° C. and stirred at room temperature for 2 hours. To the reaction mixture, Amberlist 15 (trademark) (15.1 mg) was added and stirred to neutralize it. Insolubles were filtered off and the solvent was distilled to obtain the compound (26) (432.6 mg, 96.7%).

(The compound (26))

| Analysis ($C_{69}H_{77}NO_{16}$ = 1176.38) | | |
|---|---|---|
| | Calcd. | Found. |
| C | 70.45 | 70.18 |
| H | 6.60 | 6.52 |
| N | 1.19 | 1.24 |

RF 0.47 ($CHCl_3$—MeOH=19:1).
$[α]_D^{19}$+9.35°(C=0.15, $CHCl_3$).

Reference Example 5

The compound (26) (330 mg, 0.28 mmole), benzaldehyde dimethyl acetal (47 mg, 0.31 mmole), p-toluenesulfonic acid monohydrate (5 mg) and acetonitrile (5 ml) were stirred at room temperature for 5.5 hours, thereafter triethylamine (0.5 ml) was added. The reaction mixture was concentrated. The residue was subjected to column chromatography and eluted with toluene-ethyl acetate (1:1, v/v) to obtain the compound (27) (332 mg, 93.4%).

(The compound (27))

| Analysis ($C_{76}H_{81}NO_{16}$ = 1264.49) | | |
|---|---|---|
| | Calcd. | Found. |
| C | 72.19 | 72.39 |
| H | 6.46 | 6.51 |
| N | 1.11 | 1.05 |

RF 0.48 (toluene - EA=1:2).
$[α]_D^{19}$ +28.24°(C=0.17, $CHCl_3$).

Reference Example 6

To well dried molecular sieves 4A powder (1 g), a solution (5 ml) of $Hg(CN)_2$ (126.3 mg, 0.5 mmole) and the compound (27) (316.1 mg, 0.25 mmole) in dry benzenenitromethane (1:1, v/v) was added and stirred at room temperature for one hour. A solution (5 ml) of acetobromogalactose (28) (154.2 mg, 0.375 mmole) in dry benzene-nitromethane (1:1, v/v) was dropwise added and stirred at 60° C. for 4 hours. Insolubles were filtered off and the solution was concentrated. The residue was dissolved in dichloromethane. The solution was washed with $NaHCO_3$water and saturated NaCl water and dried on $MgSO_4$. After $MgSO_4$was separated, the solvent was distilled. The residue was subjected to column chromatography and eluted with toluene-ethyl acetate (5:4, v/v) to obtain the compound (29) (387 mg, 97.1%).

(The compound (29))

| Analysis ($C_{90}H_{99}NO_{25}$ = 1594.784) | | |
|---|---|---|
| | Calcd. | Found. |
| C | 67.78 | 67.96 |
| H | 6.26 | 6.27 |
| N | 0.88 | 0.90 |

Rf 0.54 (toluene - EA=1:1).
$[α]_D^{18}$ +47.65°(C=0.17, $CHCl_3$).

Reference Example 7

A solution (20 ml) of the compound (29) (1.6 g, 1 mmole) in 80% acetic acid water was stirred at 80° C.

for 2 hours, and then concentrated. After azeotropic distillation with ethanol, the residue was subjected to column chromatography and eluted with toluene - ethyl acetate (2:3, v/v) to obtain the compound (30) (1.36 g, 90.4%).

(The compound (30))

| Analysis ($C_{83}H_{95}NO_{25} \cdot 1H_2O = 1524.689$) | | |
|---|---|---|
| | Calcd. | Found. |
| C | 65.39 | 65.45 |
| H | 6.41 | 6.34 |
| N | 0.92 | 0.85 |

Rf 0.29 (toluene - EA = 1:2).
$[\alpha]_D^{19}$ +22.67°(C=0.75, CHCl$_3$).

Reference Example 8

The compound (30) (385 mg, 0.256 mmole) was dissolved in acetic acid (15 ml). 10% Pd-C (385 mg) was added and catalytic reduction was conducted at 80° C. for 3 hours to obtain the compound (31) (TLC Rf 0.38, BuOH: EtOH:H$_2$O = 4:2:2 (v/v)). The reaction mixture was filtered to remove Pd-C and concentrated in vacuo. To the residue, acetic anhydride (5 ml) and pyridine (5 ml) were added and stirred at room temperature for one day. After concentrated in vacuo, the residue was subjected to silica gel column chromatography (Wakogel C-300, 30 g) and eluted with ethyl acetate to obtain the compound (9) (234 mg, 73.0%).

(The compound (9))

Analysis Calcd. C, 49.80, H, 5.71, N, 1.12. Found. C, 49.95, H, 5.81, N, 0.92. Rf 0.38 (EA).

Reference Example 9

The compound (25) (1.042 g, 0.8 mmole) was dissolved in acetic acid (10 ml). 10% Pd-C (200 mg) was added and catalytic reduction was conducted at room temperature for 5 hours. Pd-C was filtered off and the solution was concentrated in vacuo to obtain the compound (32) (531.1 mg, 98.8%).

Reference Example 10

The compound (32) (376.7 mg, 0.56 mmole) was dissolved in acetic acid (10 ml) and pyridine (10 ml). The mixture was stirred at room temperature for one day and further at 110° C. for 3 hours, thereafter concentrated in vacuo. The residue was subjected to silica gel column chromatography (Wakogel (trademark) C-300, 40 g) and eluted with ethyl acetate-toluene (2:1, v/v) to obtain the compound (10) (305 mg, 56.4%).

The compound (10))

Rf 0.42 (EA:toluene 2:1).
Analysis Calcd. C, 49.73, H, 5.74, N, 1.45. Found. C, 50.96, H, 5.75, N, 1.36.
NMR (CDCl$_3$ 400 MHz, $\delta$, ppm TMS) 1.95–2.48 CH$_3$CO=33H, 5.67 1H, d, 12.3 Hz, anomeric proton, 5.67, 1H, d, 12.3 Hz, anomeric proton.

Example 1

The compound (9) (210 g, 0.167 mmole) was dissolved in DMF (1.0 ml) and heated to 50° C. Hydrazinium acetate (20.4 mg) was added. The mixture was stirred for 5 minutes, diluted with ethyl acetate and washed with saturated NaCl water. After dried on MgSO$_4$, the solution was concentrated in vacuo. The residue was subjected to silica gel column chromatography (Wakogel C-300, 12 g) and eluted with ethyl acetate to obtain the compound (4) (151 mg, 74.4%).

(The compound (4))

$[\alpha]_D^{23}$ +24.5°(C=0.67 CHCl$_3$)
Analysis Calcd. C, 49.54, H, 5.74, N, 1.16. Found. C, 49.24, H, 5.69, N, 1.05.
Rf 0.34 (EA).

Example 2

The compound (4) (128 mg, 0.106 mmole) was dissolved in methylene chloride (0.5 ml). Trichloroacetonitrile (61 mg) and NaH (5 mg) were added. The mixture was stirred for 1.5 hours under ice-cooled condition at an argon atmosphere. The reaction mixture was concentrated in vacuo and subjected to silica gel column chromatography (Wakogel C-300, 12 g) and eluted with ethyl acetate to obtain the compound (3) (75 mg, 52.4%).

(The compound (3))

Rf 0.50 (EA).
PMR (90 MHz, CDCl$_3$ ppm, TMS) 1.96, 2.04, 2.11, 2.16, CH$_3$CO×13 6.48, 1Hd J=4.8 H-1a 8.64, S,>C=NH.

Example 3

The compound (3) (75 mg, 0.056 mmole) and the compound (12) (42 mg, 0.056 mmole) were dissolved in chloroform. Activated molecular sieves 4A (0.5 g) and BF$_3$•Et$_2$O (9 μl) were added under ice-cooled condition at an argon atmosphere. The mixture was stirred at that temperature for 4 hours and then at room temperature for one day, and diluted with chloroform, filtered through Celite (trademark) and concentrated in vacuo. The residue was subjected to silica gel column chromatography (Wakogel C-300, 15 g) and eluted with ethyl acetate - toluene (3:1, v/v) to obtain the compound (2) (19 mg, 17.6%).

(The compound (2))

$[\alpha]_D^{23}$ +7.91°(C=0.67 CHCl$_3$)
Analysis Calcd: C, 61.03, H, 7.97, N, 1.44. Found. C, 61.26, H, 8.12, N, 1.44.
Rf 0.40 (EA:toluene=4:1).

Example 4

The compound (2) (11.1 mg, 0.0057 mmole) was dissolved in methanol (1.0 ml) and tetrahydrofuran (THF) (1.0 ml). 1N—NaOCH$_3$ (30 μl) was added. The mixture was stirred at room temperature for 5 hours. Amberlist 15 (trademark) was added to neutralize the mixture, which was then concentrated in vacuo. The residue was recrystallized from methanol to obtain the compound (1) (5.0 mg, amorphous powder, 65.5%).

(The compound (1))

Rf 0.58 (n—BuOH—EtOH—H$_2$O=4:2:2).
$[\alpha]_D^{25}$ +2.5°(C=0.25, CHCl$_3$:MeOH=1:1).
PMR (400 MHz, Me$_2$SO d-6-D$_2$O (98:2 v/v) ppm (TMS)) 0.85, t, J=6.84, —CH$_3$×2, 1.23, 62H, —CH$_2$—, 1.43, m, H-6', 1.83, s, NHCOCH$_3$, 1.92, m, H-3", 2.02, t, J=7.32, H-2", 4.21, d,J=7.33, H-1b, H-1c, 4.56, d, J=8.31, H-1d.

Example 5

The compound (10) (113 mg, 0.117 mmole) was dissolved in DMF (0.5 ml) and heated to 50° C. Hydrazinium acetate (13 mg) was added and stirred for 5 minutes. The reaction mixture was diluted with ethyl acetate, washed with saturated NaCl water, dried on MgSO4 and concentrated in vacuo. The residue was subjected to silica gel column chromatography (Wakogel C-300, 10 g) and eluted with toluene-ethyl acetate (1:2, v/v) to obtain the compound (8) (61.0 mg, 56.4%).

(The compound (8))

$[\alpha]_D^{25}$ +21.4 (C=0.5, CHCl3).
Analysis Calcd. C, 49.40, H, 5.78, N, 1.52. Found. C, 49.75, H, 5.74, N, 1.36.

Example 6

The compound (8) (58 mg, 0.063 mmole) was dissolved in methylene chloride (0.5 ml). Trichloroacetonitrile (36 mg) and NaH (60% in oil) (3.0 mg) were added under ice-cooled condition and stirred for 1.5 hours at an argon atmosphere. The reaction mixture was concentrated in vacuo. The residue was subjected to silica gel column chromatography (Wakogel C-300, 5 g) and eluted with toluene - ethyl acetate (1:2, v/v) to obtain the compound (7) (46 mg, 67.1%).

(The compound (7))

TLC Rf 0.45 (toluene - EA = 1:2).
PMR (90 MHz, CDCl3, ppm, TMS) 1.96, 2.01, 2.05, 2.11, 2.16, 2.36, 2.43, 2.48, CH3COO × 10, 6.47 d J=5.0 H-1a, 8.64, s, >=NH.
CMR (22.5 MHz, CDC 3, ppm) 93.03 C-1a, 98.55, C-1b, 100.99, C-1c CDCl3.

Example 7

The compound (7) (46 mg, 0.043 mmole) and the compound (12) (32 mg, 0.043 mmole) were dissolved in chloroform (1.0 ml). Under ice-cooled condition and at an argon atmosphere, activated molecular sieves 4A (0.5 g) and BF3•Et2O (7 μl) was added. The mixture was stirred at that temperature for 4 hours and further at room temperature for one day. The reaction mixture was filtered through Celite (trademark) and insolubles were washed with chloroform. The washing solution and the filtrate were combined and concentrated in vacuo. The residue was subjected to silica gel column chromatography (Wakogel C-300, 12 g) and eluted with toluene - ethyl acetate (5:4, v/v) to obtain the compound (6) (27.1 mg, 37.9%).

(The compound (6))

Rf 0.66 (toluene - EA = 1:2).
$[\alpha]_D^{23}$ +2.62 (CHCl3 C=1.41).
Analysis Calcd. C, 62.94, H, 8.38, N, 1.68. Found. C, 62.34, H, 8.18, N, 1.66.
PMR (400 MHz, CDC 3, ppm, TMS) 0.88 t, J=6.35, CH3—×2, 1.25, s, —CH2—×32, 1.60, bs, 2H, —CH-2CO, 1.94-2.46, CH3CO×10, 7.42-8.01, 5H, m, aromatic proton.

Example 8

The compound (6) (20.0 mg, 0.012 mmole) was dissolved in methanol (1 ml) and tetrahydrofuran (1 ml). 1N—NaOCH3 (0.12 ml) was added and stirred at room temperature for 5 hours. The reaction mixture was neutralized by Amberlist 15 (trademark), filtered and concentrated in vacuo. The residue was recrystallized from methanol to obtain the compound (5) (9.9 mg, amorphous powder, 69.8%).

(The compound (5))

Rf 0.62 (n—BuOH:EtOH:H2O=4:2:2).
$[\alpha]_D^{20}$ −2.8°(C=0.5, CHCl3:CH3OH=1:1).
PMR (400 MHz, Me2SO d-6-D2O (98:2 v/v) ppm, TMS) 0.85, t, J=6.59, CH3—×2, 1.23, 62H, —CH2—, 1.42, m, H—3″, 1.88, s, NHCOCH3, 2.02, t, J=7.33, 1.92, m, H—b′, 3.03, t, J=7.81, H-2a, 4.16, J=7.08, H1a, 4.21, J=7.57, H-1b, 4.46, J=8.54, H-1c.

What we claim is:

1. An asialoganglioside related compound of the formula (I):

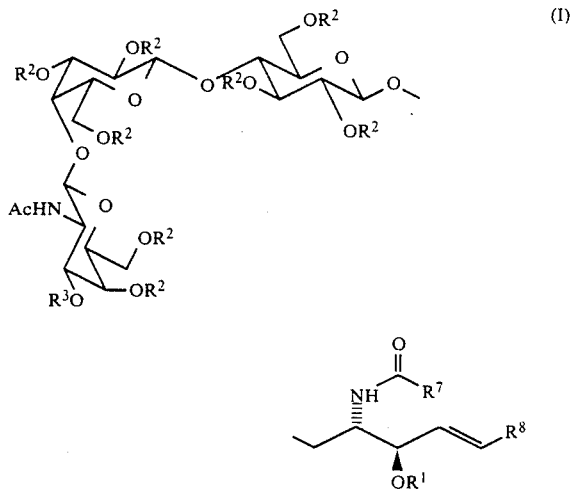

wherein $R^1$ is benzoyl, $R^2$ is acetyl, $R^3$ is acetyl or 2, 3, 4, 6-tetra-O-acetyl-β-galactopyranosyl, $R^7$ and $R^8$ are individually alkyl having 1 to 30 carbon atoms and Ac is acetyl.

2. The compound of claim 1, wherein $R^3$ is acetyl.

3. The compound of claim 1, wherein $R^3$ is 2, 3, 4, 6-tetra-O-acetyl-β-D-galactopyranosyl.

4. The compound of claim 1, wherein $R^7$ is $C_{23}H_{47}$ and $R^8$ is $C_{13}H_{27}$.

5. The compound of claim 2, wherein $R^7$ is $C_{23}H_{47}$ and $R^8$ is $C_{13}H_{27}$.

6. The compound of claim 3, wherein $R^7$ is $C_{23}H_{47}$ and $R^8$ is $C_{13}H_{27}$.

* * * * *